United States Patent [19]

Maruyama et al.

[11] Patent Number: 4,616,120

[45] Date of Patent: Oct. 7, 1986

[54] MICROWAVE-HEATING APPARATUS HAVING MEANS FOR MEASURING REFLECTION COEFFICIENT UNDER LOW POWER OPERATION

[75] Inventors: Yuji Maruyama, 1565-59, Notuke-machi, Tadasaki-shi, Gumma-ken; Kohei Otake, Kawagoe; Hisao Kizaki, Kamifukuoka, all of Japan

[73] Assignees: Yuji Maruyama; New Japan Radio Co. Ltd., both of Japan

[21] Appl. No.: 755,386

[22] Filed: Jul. 16, 1985

[30] Foreign Application Priority Data

Jul. 31, 1984 [JP] Japan .................... 59-160838

[51] Int. Cl.⁴ ............................................ H05B 6/68
[52] U.S. Cl. ........................ 219/10.55 A; 219/10.55 B; 219/10.55 F; 324/58 B; 324/58.5 B
[58] Field of Search ............... 219/10.55 A, 10.55 B, 219/10.55 R, 10.55 M, 10.55 F; 324/58 B, 58 C, 58.5 B, 58.5 C; 333/271, 233

[56] References Cited

U.S. PATENT DOCUMENTS

| | | | |
|---|---|---|---|
| 3,439,431 | 4/1969 | Heidtmann | 219/10.55 B |
| 3,461,401 | 8/1969 | Williams | 219/10.55 B X |
| 4,207,452 | 6/1980 | Arai | 219/10.55 A |
| 4,259,561 | 3/1981 | Roussy et al. | 219/10.55 A |
| 4,324,965 | 4/1982 | Naumann et al. | 219/10.55 A |
| 4,334,136 | 6/1982 | Mahan et al. | 219/10.55 B |
| 4,520,250 | 5/1985 | Ishihara et al. | 219/10.55 B |

Primary Examiner—Philip H. Leung
Attorney, Agent, or Firm—Armstrong, Nikaido, Marmelstein & Kubovcik

[57] ABSTRACT

A microwave-heating apparatus comprising a high-power microwave oscillator which rises in its output power in a shorter time required than a time for irradiating a testing animal, a waveguide connected to the high-power microwave oscillator, a measuring member for measuring reflection coefficient connected to the waveguide and capable of being separated from the waveguide, an impedance matching part connected to the output part of the waveguide, an applicator formed by a short-circuited tapered rectangular waveguide connected to the output part of the impedance matching part, and a container for fixing a head of the animal which is inserted as a load peeping into the applicator through an insertion port provided in the wall of the applicator, whereby the measuring member for measuring reflection coefficient operates while the high-power microwave oscillator is switched off. According to the apparatus, the heads of animals can be heated under the same heating condition so as to obtain repeatable data.

4 Claims, 9 Drawing Figures

MICROWAVE-HEATING APPARATUS HAVING MEANS FOR MEASURING REFLECTION COEFFICIENT UNDER LOW POWER OPERATION

BACKGROUND OF THE INVENTION

The present invention relates to a microwave-heating apparatus for irradiating microwave power to an animal to be tested in the biochemical field. In such an apparatus, enzymes in cells of the brain of the animal are inactivated in a moment by microwave irradiation.

Figure 1:
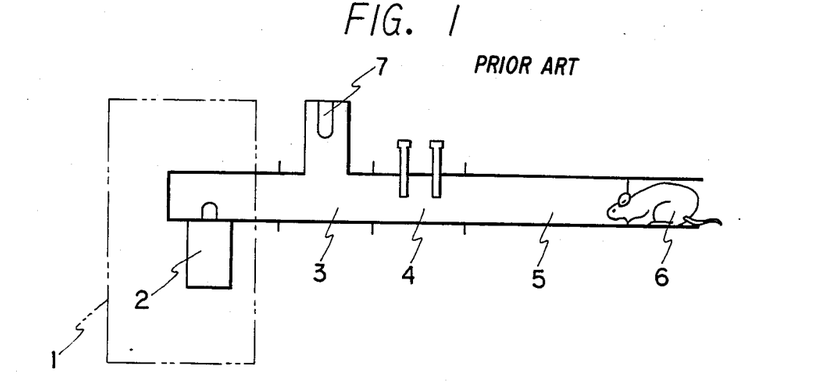
FIG. 1 is a diagram for explaining the principle of a conventional microwave-heating apparatus.

Hitherto, there has been known, as shown in FIG. 1, method where a microwave power is generated from a magnetron 2 in a high-power microwave oscillator 1. The microwave power is transmitted through a circulator 3 and coupler 4, to be applied to an animal 6 in an applicator 5 for heating a brain of the animal 6.

The microwave power which has not been absorbed into the animal 6 returns to circulator 3, turns to an absorber in 7 at that place and then is absorbed to be absorber 7.

In such a microwave-heating apparatus, impedance matching is obtained by adjusting matching devices in a matching section 4 under high-power microwave output emitted from oscillator 1 for a standard test animal (e.g. a rat of 300 g). Thereafter, the matching section 4 is locked. Therefore, real matching cannot be performed for each specific animal put to use. This is because an impedance matching performed for each test animal would a harmful influence on the animal since the animal is heated with high-power microwave output supplied from the high-power microwave oscillator 1.

Though it might be possible to supply a low-power microwave output by means of lowering the power of the magnetron, a procedure for lowering the power of the magnetron is fairly severe. Besides, even if such a procedure is forcibly done, it causes a large energy loss.

In addition, the weight of an animal, taking as an example a rat, ranges from 100 g to 500 g. Therefore, the impedance matching state is varied at 100% to 80% in absorption factor. Moreover, even if rats of the same weight are employed, since the inserting states to the applicator 5 are different in every test, the absorption factor is varied further more. Therefore, it results in underheating or overheating of a rat. The latter case often results in destruction of the brain tissue of a rat and, as a result, poses an obstacle to the research.

On the other hand, the appropriate irradiation time (the term "irradiation time" means the time period of power irradiation required for obtaining the desired heating effect on a test animal) for heating a small animal, such as a mouse, is as short as 300 ms to 500 ms. However, the rise time of a microwave power (the term "rise time" means the time period required for coupling of the full radiated output power to the load) is conventionally 300 ms to 500 ms, that is to say, the irradiation time and the rise time are almost the same. Further, the microwave power does not exhibit constant value at every rise time, but rather it exhibits an unstable value.

Accordingly, the heating condition does not remain in a constant state, since the proportion of the rise time to the irradiation time is so great.

As described above, in a conventional microwave-heating apparatus, the impedance matching could not be obtained for every animal actually used. The heating condition could not be constant because the rise time of the microwave power was too long, so that repeatable data could not be obtained.

An object of the present invention is to provide a microwave-heating apparatus capable of heating a test animal in the same condition to obtain repeatable data.

SUMMARY OF THE INVENTION

In accordance with the present invention, there is provided a microwave-heating apparatus comprising a high-power microwave oscillator which rises in a shorter time than a time for irradiating a test animal, a waveguide connected to the high-power microwave oscillator, a measuring member for measuring reflection coefficient connected to the waveguide and capable of being separated from the waveguide, an impedance matching part connected to output part of the waveguide, an applicator formed by a short-circuited tapered rectangular waveguide connected to an output part of the impedance matching part, and a container for fixing a head of the animal which is inserted as a load peeping into the applicator through an insertion port provided in a wall of the applicator, whereby the measuring member for measuring reflection coefficient operates while the high-power microwave oscillator is switched off.

The above and other objects and the advantages of the present invention will become apparent from the following description with reference to the accompanying drawings.

DETAILED DESCRIPTION

In an example of the present microwave-heating apparatus, the rise time for the microwave power emitted from the high-power microwave oscillator is about 50 milliseconds, and before radiating this microwave power, low-power microwaves are radiated for measuring a matching condition for each animal, so that an impedance matching is given for every animal without causing a harmful influence on the animal.

Figure 2:
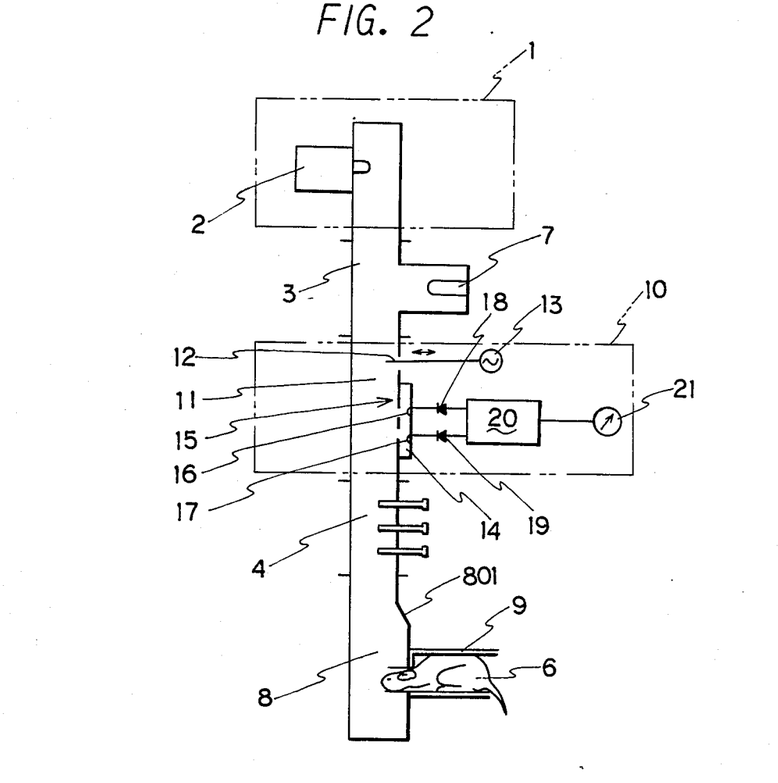
FIG. 2 is a diagram for explaining the principle of a microwave-heating apparatus of the present invention.

FIG. 2 shows a principle of the present invention, wherein the reference numerals are the same as those shown in FIG. 1.

A magnetron 2 having a rise time of about 20 milliseconds is employed in a high-power microwave oscillator 1. Applicator 8 is a rectangular waveguide gradually widened through a tapered portion 801 and it ends in a short-circuited endplate. A testing animal 6 is supported by a lossless animal holder 9 which functions as a container for fixing the test animal, and the head of the animal is inserted peeping into the applicator. The numeral 10 indicates a measuring member for measuring a reflection coefficient (VSWR monitor) to verify the impedance matching state. The measuring member is connected to a waveguide 11. The waveguide 11 is connected between a circulator 3 and a matching portion 4. For adjusting matching elements of a matched line 4, an E-H tuner, stub tuner, or the like is used.

In the measuring member 10, a coaxial antenna 12 is set up into the waveguide 11 and is capable of being taken out easily. Microwave power is supplied to antenna 12 from a low-power microwave oscillator 13. The frequency of the microwave power supplied by the low-power microwave oscillator 13 is equal to the frequency of the high-power microwave oscillator 1. The numeral 14 designates a waveguide that forms a directional coupler 15 connected to the waveguide 11, on which loops 16 and 17 are provided for detecting reflected and incident microwave powers, respectively, and which loops 16, 17 are respectively connected to a comparator 20 via crystal detectors 18 and 19.

The numeral 21 designates an indicator such as a voltmeter, ammeter or a CRT display for indicating a measured reflection coefficient. In such a way, elements 14 to 21 make up a measuring circuit for reflection coefficient.

The low-power microwave output applied to waveguide 11, from antenna 12, is divided into two microwave outputs which are radiated in different directions. One is transmitted to applicator 8. The other is transmitted to circulator 3 and is absorbed to an absorber 7. Although the most part of the former microwave power output is absorbed into the head of test animal 6, a part of the microwave power returns back to the antenna 12 as reflected wave. Those reflected and incident powers are detected by the directional coupler 15, and their levels are compared with each other in the comparator 20. Then, the compared result is indicated by the indicator 21 as a reflection coeffcient. The reflection coefficient $\Gamma$ (Gamma) may be expressed as the ratio of reflected power to incident power (i.e., $\Gamma$=reflected power/incident power), and thus the reflection coefficient can be obtained by comparing reflected power to incident power.

Then, the matching element in matched line 4 is adjusted so as to let the reflection coefficient be the smallest. That is to say, the amount of the reflected power is the smallest. As a result, the impedance matching can be obtained with respect to the present test animal 6 which is inserted into the applicator.

Thereafter, the whole measuring member 10 is electromagnetically separated (i.w., isolated) from the waveguide 11. That is to say, the antenna 12 and successively the whole of the members of the measuring circuit 14 to 21 are separated from the waveguide 11.

When microwave power for heating a test animal 6 is applied from the high-power microwave oscillator 1, the microwave power is fully absorbed to the animal 6 so that the animal is efficiently heated.

The level of microwave power can be changed by changing the microwave power from the high-power microwave oscillator 1. The operation for changing the power can be continuously performed, or can also be performed in steps, and the supplying time of a microwave power can be optionally determined by using a timer. In any case, the rise time of the microwave power can be sufficiently shortened in comparison with a time for irradiation an animal. Then, the applying power is locked and is not changed during the irradiation.

Figure 3:
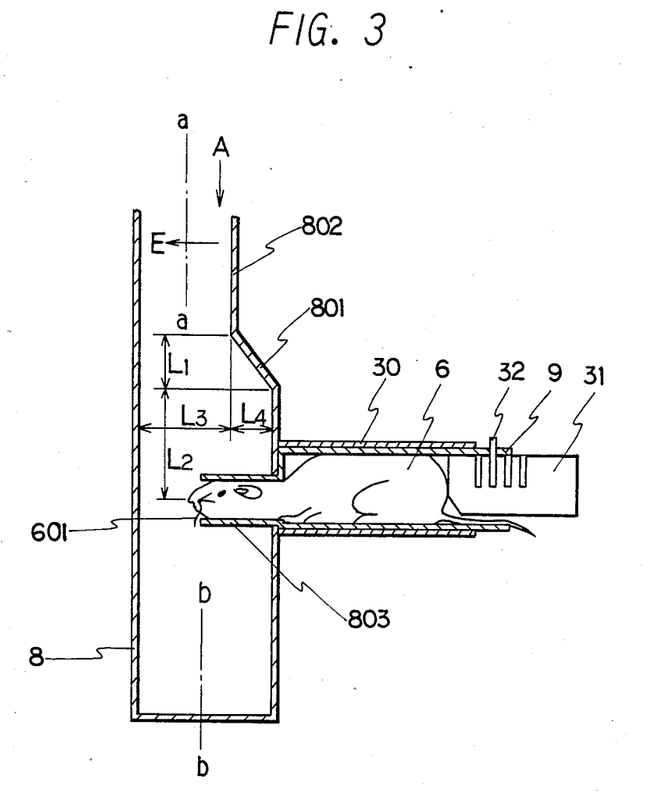
FIG. 3 is a sectional view of an applicator in a microwave-heating apparatus of the invention.

FIG. 3 shows a sectional view of the applicator 8 in detail. Microwave power travelling through the applicator 8 concentrates, essentially, to a sharpened portion of the dielectric material. An example of such a sharpened portion is a nose of the testing animal. Thus, a part of the brain, e.g. a cerebellum, is hardly heated compared with the sharpened part of the head of the animal.

In the embodiment of the microwave-heating apparatus of the invention, the above-described tapered portion 801 expands a narrow wall 802 of the waveguide along a microwave travelling direction. An insertion portion 803 is formed on the central axial line of narrow wall 802 which is expanded by the tapered portion 801. Through the port 803, a head of the testing animal can be inserted. The numeral 30 indicates a chamber for inserting an animal holder 9. The numeral 31 indicates a pushing member for pushing a testing animal into the animal holder 9. The numeral 32 indicates an engaging plate for fixing the pushing member 31 to the animal holder 9.

When microwave power of the basic $TE_{01}$ mode travels through applicator 8 in a direction of the arrow A, a gradient of the wall 802 produced by tapered portion 801 causes a displacement of the strongly heated part of the testing animal from a central line a—a of the wageguide toward the wall where the tapered portion 801 is located (toward a neck of the testing animal) along a direction of the arrow A.

Such a displacement starts from a point where the tapered portion 801 ends to a maximum height $(L_3+L_4)$. The amount of the displacement increases along a distance $L_2$ which is a distance from the end of the tapered portion 801 to a point where the dielectric material is located. The displacement of the heated part from a line a—a reaches a maximum value at some distance of $L_{2m}$. When distance $L_2$ goes beyond the above-mentioned distance $L_{2m}$, the displacement decreases, so that the strongly heated part returns to a central line b—b of the wall of the waveguide.

There cannot be uniquely determined values such as the distance $L_{2m}$ which provides the maximum displacement toward the wall 802, the area of the heated part of the testing animal, and the heating temperature. These values depend on a length $L_1$ of the tapered portion 801, a length $L_3$ of the dimension of the waveguide at the junction point of the applicator 8, a broadened length $L_4$ provided by the tapered portion 801, an inner diameter of the opening 803, a dielectric loss of the testing animal 6, a wave length of the microwaves, and the like.

In order that the head of the testing animal is uniformly heated, a distance from the finished end of the tapered portion 801 to the port 803 is not necessarily equal to the distance $L_{2m}$ in which the displacement of the strongly heated part reaches the maximum value. The distance is experimentally determined but it should not be more than $2\lambda g$ (where $\lambda g$ represents a wavelength of the used microwaves in the waveguide). The above-mentioned distance $L_4$ can be increased to an extent as long as the microwave mode in the applicator 8 is maintained in the basic $TE_{10}$ mode.

When the optimum distances $L_1$ to $L_4$ are introduced to the applicator 8 in the above-described manner, the microwave power does not concentrate on the nose of the testing animal 6, and a suitable uniform heating of the brain of the testing animal is realized. Further, since the inner dimension of the extended wall ($L_3+L_4$) in the applicator 8 is larger than the dimension $L_3$ of the wall at the junction point of the applicator, generation of an electric discharge can be prevented. The distance will be generated by a contact of whiskers 601 of the testing animal with the inner wall of the applicator 8.

In an experiment, a good result was obtained under the following conditions, $\lambda g=148$ mm; $L_1=50$ mm; $L_2=110$ mm; $L_3=54.6$ mm; $L_4=29.4$ mm; the inner diameter of the opening $803=45$ mm; the longer dimension of the applicator $8=109.2$ mm; and the microwave power=5 kW.

Figure 4:
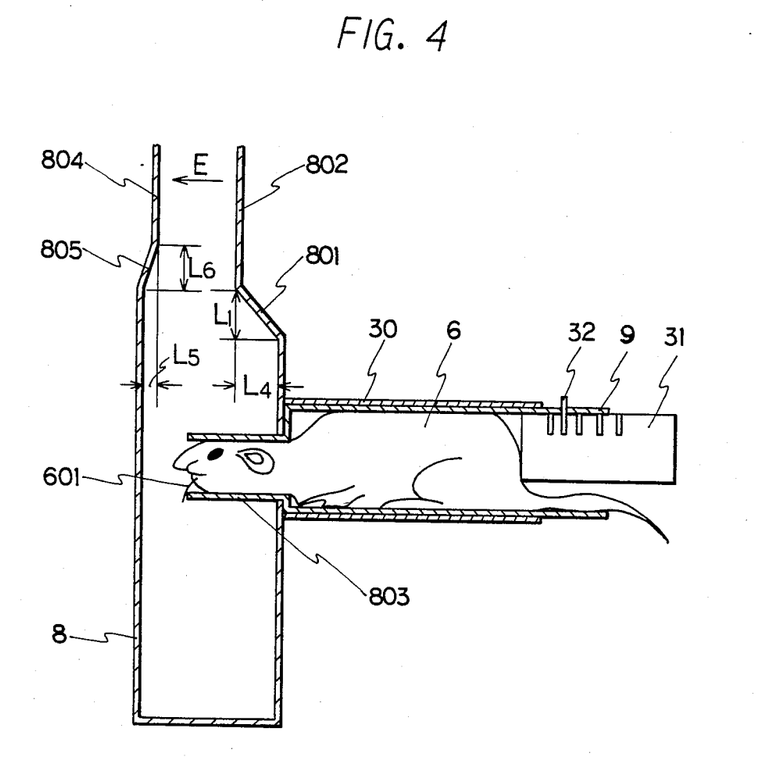
FIG. 4 is a sectional view of another example of the applicator in FIG. 3.

FIG. 4 shows another example of the applicator 8 in FIG. 3. Another tapered portion 805 is also formed on the opposite wall 804 to expand the inner space of the applicator 8. In FIG. 4, an extended length $L_5$ from the wall 804, a length $L_1$ of the tapered portion 801, a length $L_6$ of tapered portion 805 and a relative location of both tapered portions 801 and 805 are respectively determined so that the heated part in the testing animal is distributed most uniformly.

In the arrangement of FIG. 4, the inner dimension of the applicator 8 is larger than the dimension $L_5$, so that it is possible to heat a larger animal.

The heated part of the head of the testing animal can be suitably distributed by setting the distances, such as $L_1$, $L_2$, $L_4$, and the like.

Figure 5:
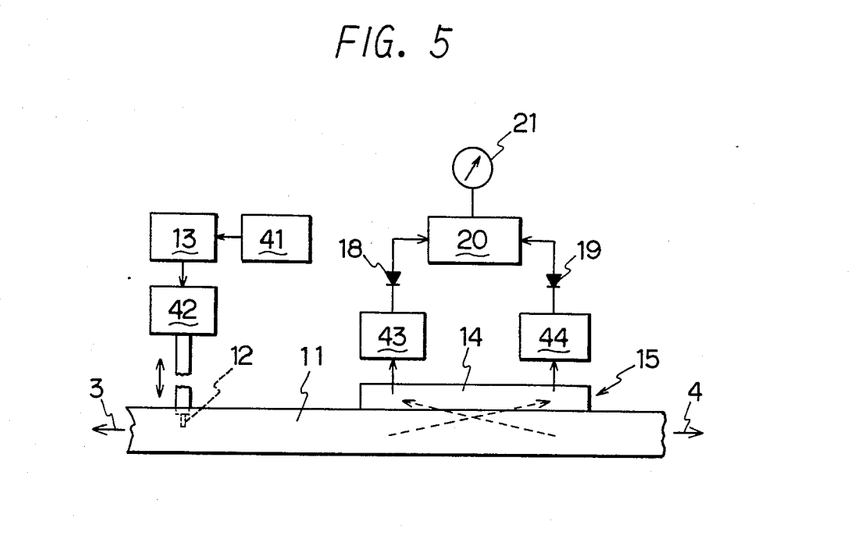
FIG. 5 is a block-diagram of a means for measuring a reflection coefficient of the microwave-heating apparatus of the invention.

FIG. 5 shows a detailed diagram of the measuring member 10 for measuring reflection coefficient. A low-power microwave oscillator 13 is connected to an amplitude modulator 41, so that the amplitude of the electric power can be modulated. The generated power is provided to an antenna 12 through an attenuator (or isolator) 42. Amplifiers 43 and 44 are connected to the output portions of the waveguide 14 which construct a directional coupler 15. Amplifiers 43 and 44 amplify the detected power for detectors 18 and 19 so as to supply an intense signal when the sensitivities of the detectors are low.

In the embodiment, the attenuator 42 attenuates the reflected power which is returned back from the antenna 12. The role of the antenuator 42 is, in the embodiment, to prevent the low-power microwave oscillator 13 from being in an unstable state.

The directional coupler 15 detects an incident power from the antenna 12 and reflected power turned back from the applicator 8. Both detected powers are respectively amplified by the amplifiers 43 and 44, detected by the detectors 18 and 19, and compared by the comparator 20. The lack of detection sensitivity (e.g. the frequency response is not good in the higher region) of the detectors 18 and 19 is compensated by amplitude-modulating the electric power with a frequency of about 1 KHz in the modulator 41.

Figure 6:
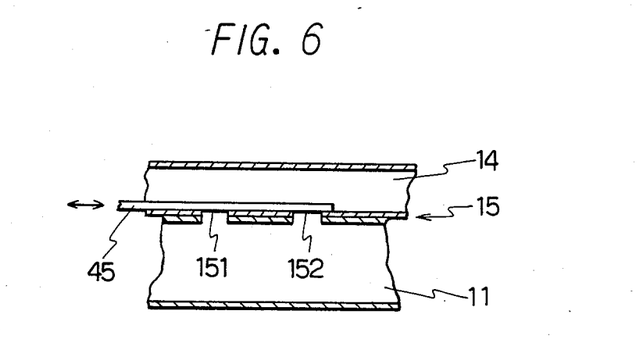
FIG. 6 is a sectional view of another example of a part of the directional coupler in FIG. 5.
Figure 7:
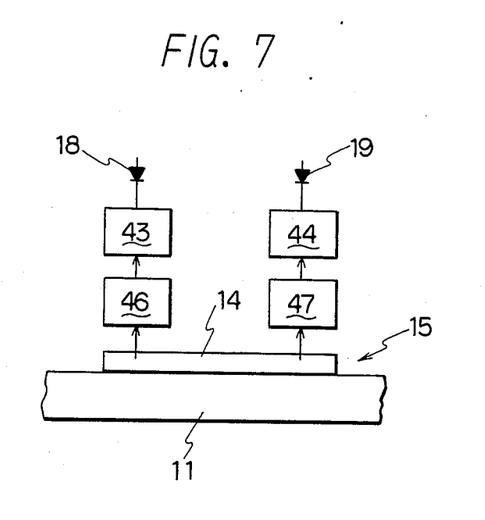
FIG. 7 is a block-diagram of another example in the output part of the directional coupler in FIG. 5.

After an impedance matching is performed, the antenna 12 is separated from the waveguide 11 by pulling it out so as to protect the low-power microwave oscillator 13. Hereafter, the parts 14 to 21 are also electromagnetically separated from the waveguide to protect the measuring circuit from the high-power microwave output. The electromagnetic separation of the parts 14 to 21 is obtained by changing a degree of coupling of the directional coupler so as to reduce the coupling coefficient. However, it sometimes occurs that the electric powers to the amplifiers 43 and 44 cannot be attenuated below a limited value for the amplifiers. This is because of the relationship among the amplification capability of the amplifiers 43 and 44, detection sensitivity of the detectors 18 and 19, the output power of the low-power microwave oscillator 13, and the like. When the electric powers cannot be reduced below the limited value, the holes 151 and 152 of the directional coupler 15 can be closed by a shutter-plate 45 as shown in FIG. 6. Also, as shown in FIG. 7, an insertion of switching circuits 46 and 47 such as pin switches (pin attenuators) may be used between the amplifiers and the directional coupler. The switching circuits 46 and 47 are closed (not conducting) while the high-power microwave output is supplied.

Figure 8:
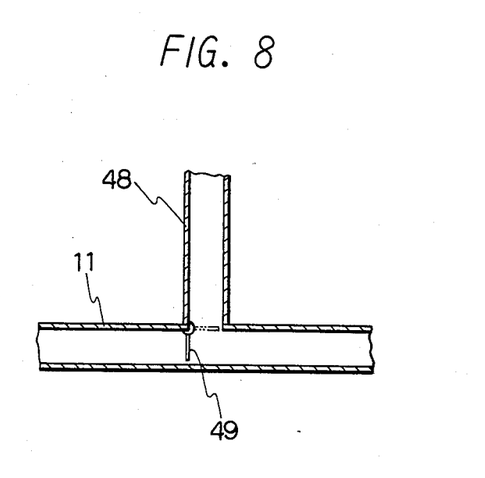
FIG. 8 is a sectional view of a modification of the antenna in FIG. 5.

In the above-described embodiment, a low-power microwave output is supplied from a coaxial cable antenna 12 by inserting it into a waveguide 11. On the other hand, as shown in FIG. 8, a waveguide 48 connected to the low-power microwave generator 13 can be provided on the waveguide 11. In the arrangement of FIG. 8, the connection between the waveguide 48 and the waveguide 11 is controlled by a shutter-plate 49. That is to say, the shutter-plate 49 is located in such a manner that it shuts the waveguide 11 (shown in a full line of FIG. 8) so as to enable performing a verification or an adjustment of the impedance matching by supplying a low-electric power output. In the other case, when the shutter-plate 49 is located in such a manner that it shuts the waveguide 48 (shown in an imaginary line of FIG. 8), low-power microwave oscillator 13 is separated from the waveguide 11, and a high electric power output is supplied to the applicator 8. In the above embodiment, when a coaxial line is used for microwave transmission instead of the waveguide 11, a switch can be used to switch the coaxial line and the coaxial antenna 12.

Figure 9:
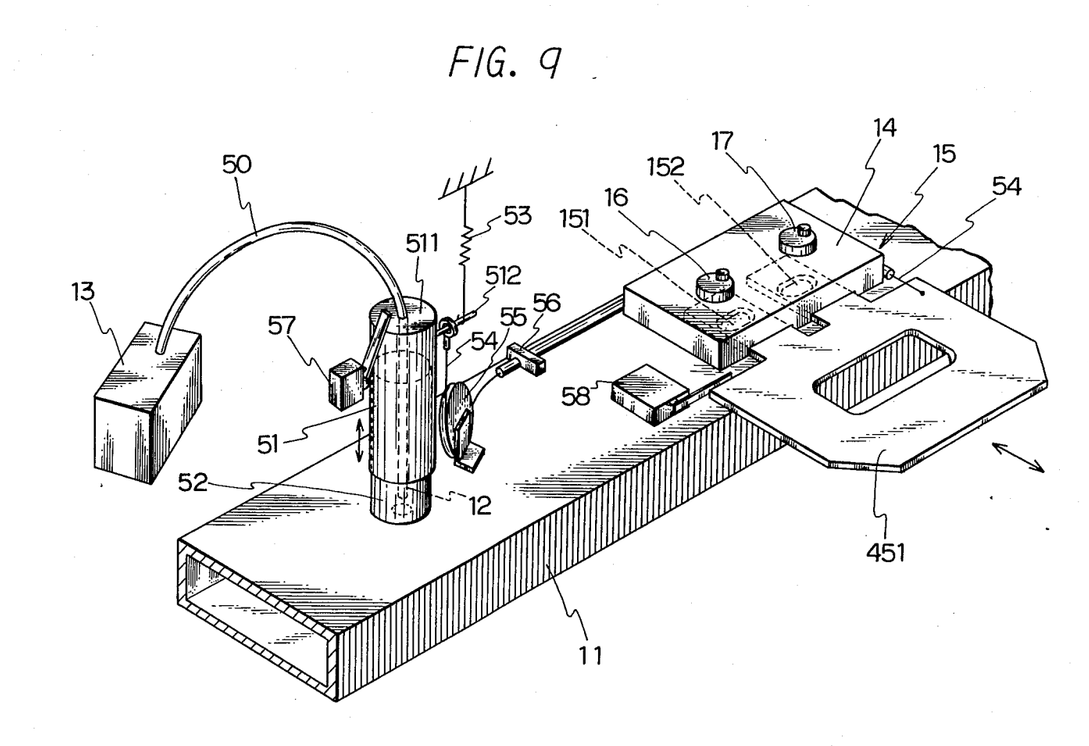
FIG. 9 is a perspective view showing a combination of a shutter plate and an antenna of the directional coupler.

In FIG. 9, there is shown a mechanism which combines movement of coaxial antenna 12 and a shutter-plate 451. The shutter-plate 451 is used for shutting the holes 151 and 152 of the directional coupler 15. In FIG. 9, the shutter-plate 451 is, instead of the shutter-plate 45 in FIG. 6, adapted to move in a direction perpendicular to a direction passing through the hole 151 and the hole 152. The coaxial cable 50, which becomes a feeder line of the antenna 12, is fixed to the endplate 511 of the outer tubular body 51 which can be inserted into an inner tubular body 52. The body 52 is provided on the waveguide 11. The numeral 512 indicates a pin provided on the side surface of the outer tubular body 51. The numeral 53 indicates a spring used for upwardly pulling the outer tubular body 51. The numeral 54 indicates a wire, one end of which is engaged with the pin 512, and the other end of the wire 54 is engaged with the shutter-plate 451 through a pulley 55 which is provided on the outer surface of the waveguide 11. The wire 54 is covered with an outer casing which is fixed by a member 56 on the waveguide. The numeral 57 indicates a microswitch for detecting the position of the antenna 12. The numeral 58 indicates another microswitch used for detecting the position of the shutter-plate 451.

In the mechanism of FIG. 9, when the holes 151 and 152 are opened by pulling-out the shutter-plate 451, the antenna 12 is inserted into the interior of the waveguide 11. At the same time, the microswitches 57 and 58 are switched off. Therefore, when the holes 151 and 152 are closed by pushing-in the shutter-plate, the antenna 12 is moved backwardly and comes out of the interior of the waveguide 12. At the same time, the microswitches 57 and 58 are switched on.

The microswitches 57 and 58 can be connected in series to a starter of the high-power microwave oscillator 1. By pulling-out the shutter-plate 451, the high-power microwave oscillator 1 is switched off, and only the measuring member 10 in FIG. 2 is operated. On the other hand, when the shutter-plate 451 is pushed-in, the antenna 12 is pulled up and the holes 151 and 152 are closed, and then the measuring member 10 stops its operation, and the high-power microwave oscillator 1 is switched on, so that the heating with microwave power is carried out.

According to the present invention, the instability of heating can be avoided because the rise time of the output power of the oscillator is shorter than the time required to apply the microwave power to the testing animal. Further, according to the present invention, heating of each testing animal is performed efficiently by matching the impedance without influencing any effect on the testing animal before heating it. Furthermore, the head of the animal is uniformly heated by using an applicator whose narrow wall is extended by a tapered portion.

Accordingly, the head of each animal can be heated under the same heating condition, so as to obtain repeatable data.

What we claim is:

1. A microwave-heating apparatus having means for measuring reflection coefficient under low power operation, comprising:

a high-power microwave oscillator;

a waveguide connected to an output of the high-power microwave oscillator;

means for measuring reflection coefficient connected to one wall of the waveguide;

impedance matching means connected to an output of the waveguide;

an applicator formed by a short-circuited rectangular waveguide tapered at one wall thereof and connected to an output of the impedance matching means and having an insertion port for inserting a load therein in the one wall of the tapered rectangular waveguide; and a container, for holding a test animal disposed at the insertion port of the applicator; wherein the means for measuring reflection coeffcient comprises a low-power microwave oscillator connected to an antenna which can be inserted into or withdrawn from the one wall of the waveguide so as to be connected to or separated from the waveguide, connecting holes formed in the one wall of the waveguide for introducing an incident power supplied from the low-power microwave oscillator and a reflected power returned back from a load, a shutter-plate for covering the connecting holes when a high-power microwave output is supplied from the high-power microwave oscillator, and a comparator for comparing the incident power with the reflected power.

2. The microwave-heating apparatus of claim 1 wherein the high-power microwave oscillator functions in such a manner that the time period required for coupling of the full radiated output power to the load is shorter than the irradiation time period required for obtaining a desired heating effect on the test animal.

3. The microwave-heating apparatus of claim 1 wherein the applicator has a tapered portion on the one wall of the rectangular waveguide and the insertion port is provided on a center line of the one wall of the rectangular waveguide at a place in the rectangular waveguide not more that two times a wavelength of the used microwaves from a finished end of the tapered portion.

4. The microwave-heating apparatus of claim 1, wherein the low-power microwave oscillator is connected to an amplitude modulator whereby the electric power output of the low-power microwave oscillator is amplitude-modulated.

* * * * *